United States Patent
Li et al.

(10) Patent No.: US 7,418,076 B2
(45) Date of Patent: Aug. 26, 2008

(54) SYSTEM AND METHOD FOR CROSS TABLE TOMOSYNTHESIS IMAGING FOR TRAUMA APPLICATIONS

(75) Inventors: Baojun Li, Waukesha, WI (US); Renuka Uppaluri, Pewaukee, WI (US); Carson Hale Thomas, Brookfield, WI (US); Gerald Paul Schulte, Onocomowoc, WI (US); Gopal B. Avinash, New Berlin, WI (US); Rowland F. Saunders, Hartland, WI (US); Tammy M. Merisotis, Surfside Beach, SC (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/280,151

(22) Filed: Nov. 16, 2005

(65) Prior Publication Data
US 2007/0110212 A1    May 17, 2007

(51) Int. Cl.
*A61B 6/00* (2006.01)
(52) U.S. Cl. ...................................................... 378/26
(58) Field of Classification Search ................. 378/147, 378/150, 151, 154, 155, 4–27
See application file for complete search history.

(56) References Cited

U.S. PATENT DOCUMENTS

| | | | | |
|---|---|---|---|---|
| 5,095,501 A * | 3/1992 | Kobayashi | .................. | 378/196 |
| 5,187,659 A | 2/1993 | Eberhard et al. | ............... | 378/9 |
| 5,483,960 A * | 1/1996 | Steiger et al. | ............... | 600/425 |
| 6,263,041 B1 * | 7/2001 | Van Der Ende | ............... | 378/21 |
| 6,292,534 B1 * | 9/2001 | Linders et al. | ............. | 378/98.2 |
| 6,438,210 B1 * | 8/2002 | Castleberry | .................. | 378/154 |
| 6,854,140 B2 * | 2/2005 | Bartels et al. | .................. | 5/601 |
| 6,901,132 B2 | 5/2005 | Eberhard et al. | ............. | 378/23 |
| 6,970,531 B2 * | 11/2005 | Eberhard et al. | ............. | 378/26 |
| 7,082,184 B2 * | 7/2006 | Tsujii | ......................... | 378/21 |
| 2005/0041768 A1 | 2/2005 | Li et al. | ........................ | 378/2 |

OTHER PUBLICATIONS

D.G. Grant, "Tomosynthesis: A three-dimensional radiographic imaging technique" IEEE Trans on Biomedical Engineering, vol. BME-19, No. 1 Jan. 1972, pp. 20-28.
J.T. Dobbins, III, R.L. Webber, S.M. Hames, "Tomosynthesis for improved pulmonary nodule detection" Radiology/RSNA abstract No. 604, p. 280, vol. 290(P) (1998).

(Continued)

*Primary Examiner*—Courtney Thomas
(74) *Attorney, Agent, or Firm*—McAndrews, Held & Malloy, Ltd.; Peter J. Vogel; Michael A. Dellapenna

(57) ABSTRACT

The presently described technology provides a tomosynthesis imaging system that comprises an x-ray tube and an anti-scatter grid. The x-ray tube is configured to emit x-rays from a plurality of positions during movement of the x-ray tube along a long axis of a mobile patient surface. The anti-scatter grid is configured to filter out scattered x-rays and includes a grid line parallel to the long axis of the mobile patient surface. The x-rays emitted from the plurality of positions are reconstructed into at least one image of at least one plane of a patient anatomy. The described technology is useful in emergency or trauma applications where a patient may be quickly and easily moved on a mobile patient surface to a position near an x-ray detector used in combination with the x-ray tube and anti-scatter grid.

18 Claims, 3 Drawing Sheets

OTHER PUBLICATIONS

JNMT, Siebert and Boone 33 (1):3, Figure 10, Nov. 16, 2005, http://tech/snmjournals.org/cgi/content-nw/full/33/1/3/F10.

Mass General Hospital Department of Radiology—Breast Imaging, Nov. 3, 2005, http://www.massgeneralimaging.org/BreastImaging_Site/NewFiles.

Storming Media, Tomosynthesis Breast Imaging Early Detection and Characterization, Nov. 3, 2005, http://www.stormingmedia.us//13/1377/A137783/html.

MayoClinic.com, Digital tomosynthesis: A better mammogram?, Nov. 3, 2005, http://www.mayoclinic.com/health/digital-tomosynthesis/AN0087.

Russell, Hank, Digital Breast Tomosynthesis Adds Another Dimension, dated Apr. 26, 2005, Nov. 3, 2005, http://www.advancedimagingpro.com/article.jsp?siteSection.

Dobbins III PhD., James T., Chest Radiography, Pt. 3: Chest Tomosynthesis, May 2005, Nov. 3, 2005, http://www.imagingeconomics.com/library/200505-05.asp.

Mercury Computer Systems, Inc., Application Spotlight, Digital Breast Tomosynthesis (DBT), (2004).

Stevens, Grant M., et al., Radiology 2003:228:569-575, Circular Tomosynthesis: Potential in Imaging of Breast and Upper Cervical Spine-Preliminary Phantom and In Vitro Study, Nov. 3, 2005, http://radiology.rsnajnls.org/cgi/content/full/228/2/569.

Radiology Society of North America, RSNA 2005 Features Latest Research in fMRI, MDCT, PET/Ct and Other Modalities, Nov. 3, 2005, http://www.rsna.org/Publications,rsnanews/oct05/scientific_program.cfm.

D.G. Grant, "Tomosynthesis: A three-dimensional radiographic imaging technique" IEEE Trans on Biomedical Engineering, vol. BME-19, No. 1, Jan. 1972, pp. 20-28.

J.T. Dobbins, III, R.L. Webber, S.M. Hames, "Tomosynthesis for improved pulmonary nodule detection" Radiology/RSNA abstract No. 604, p. 280, vol. 290(P) (1998).

* cited by examiner

SYSTEM AND METHOD FOR CROSS TABLE TOMOSYNTHESIS IMAGING FOR TRAUMA APPLICATIONS

RELATED APPLICATIONS

Not Applicable.

FEDERALLY SPONSORED RESEARCH OR DEVELOPMENT

Not Applicable.

BACKGROUND OF THE INVENTION

The present invention relates generally to tomosynthesis imaging. More specifically, the invention relates to cross table tomosynthesis in a trauma application.

Tomography involves obtaining a two-dimensional image slice (or tomogram) from a three-dimensional volume. A variety of tomographic imaging techniques exist today, such as conventional linear tomography, computed axial tomography (CT), and positron emission tomography (PET).

A relatively new and promising tomographic imaging technique is tomosynthesis. Tomosynthesis allows retrospective reconstruction of an arbitrary number of tomographic planes of anatomies from a set of projection images acquired over a variety of angles. Compared to conventional linear tomography, tomosynthesis provides premium image quality and enhanced depth information at a lower x-ray dose. Image quality and depth information is, of course, important when diagnosing patients. Additionally, tomosynthesis is relatively fast and cost-effective.

For trauma patients such as accident victims, it is critical to rapidly localize the site and extent of the injury for successful treatment and rehabilitation. As victims are often unconscious, imaging of vertebra misalignment (for example, lateral view) is often required for a patient at a supine position. Conventional x-ray systems are usually present in hospital emergency rooms, and these systems can provide fast, high resolution imaging of the patient spine.

However, such systems often fail to provide views through thick parts of a patient anatomy (for example, a shoulder) or to differentiate between overlapping bony structures (for example, a skull). In addition, such systems may not localize the site of the injury in three dimensions.

CT systems have been used as a potential solution to the above problems in trauma cases. However, these systems have several shortcomings. First, these systems are not typically found in emergency rooms. Therefore, additional time is required to move a patient to a CT system. In addition, CT scanning is usually slow compared to x-ray imaging. In emergency situations, this additional time may not be available.

CT systems also typically have larger spatial resolution than an x-ray image for an image plane that is perpendicular to the x-ray direction due to re-slicing, for example. Moreover, the x-ray dose from a CT imaging system is usually much higher than for an x-ray system. For example, CT imaging systems may use doses up to 10 times or more than doses used in x-ray systems.

Thus, a need exists for an x-ray system and method that provides for fast, high resolution imaging of a patient anatomy (such as a spine or other body parts), along with three-dimensional localization of a patient injury and good contrast resolution. In addition, the above needs should be met with existing equipment found in emergency rooms.

These needs may be met using digital x-ray tomosynthesis systems and methods described herein.

BRIEF DESCRIPTION OF THE INVENTION

The presently described technology provides a tomosynthesis imaging system that comprises an x-ray tube and an anti-scatter grid. The x-ray tube is configured to emit x-rays from a plurality of positions during movement of the x-ray tube along a long axis of a mobile patient surface. The anti-scatter grid is configured to filter out scattered x-rays and includes a grid line parallel to the long axis of the mobile patient surface. The x-rays emitted from the plurality of positions are reconstructed into at least one image of at least one plane of a patient anatomy.

The presently described technology provides a method for employing tomosynthesis to image a patient anatomy. The method comprises moving an x-ray tube along a long axis of a mobile patient surface, emitting x-rays in a plurality of positions during the moving step, filtering out scattered x-rays with an anti-scatter grid that includes a grid line parallel to the long axis of the mobile patient surface, creating a plurality of projection images from the x-rays received at an x-ray detector, and reconstructing the x-rays into at least one image of at least one plane of the patient anatomy.

The presently described technology also provides a system for obtaining an x-ray image using tomosynthesis in a trauma application. The system comprises an x-ray tube, an anti-scatter grid, an x-ray detector, and a computing apparatus. The x-ray tube is configured to move along a long axis of a mobile table and to emit x-rays in a plurality of positions along the long axis. The mobile table is configured to support a patient in a supine position. The anti-scatter grid is configured to filter out scattered x-rays and includes a grid line parallel to the long axis of the mobile table. The x-ray detector is configured to receive the x-rays. The computing apparatus is configured to reconstruct at least one plane of a patient anatomy from the x-rays emitted in the plurality of positions.

Figure 1:
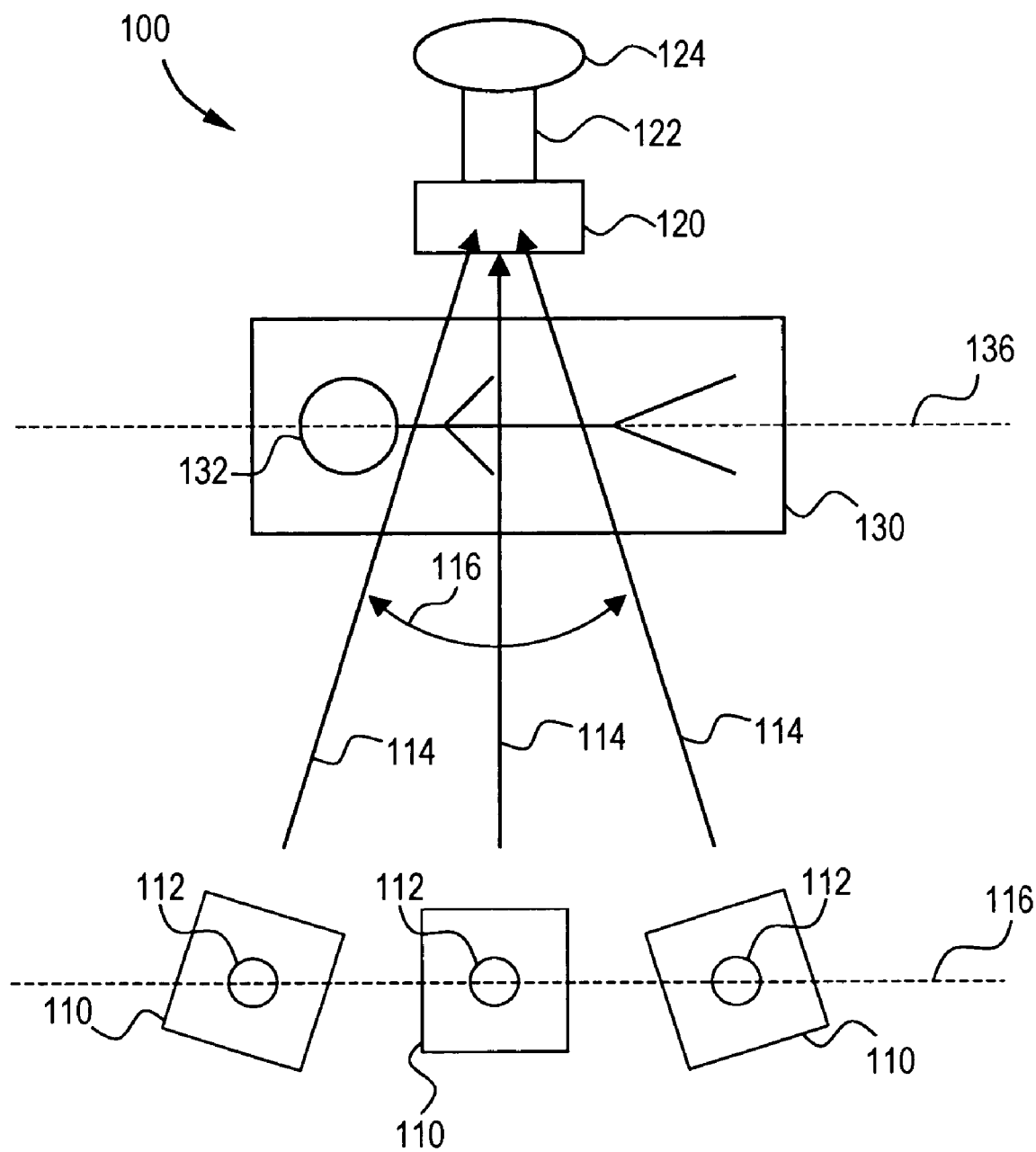
FIG. 1 illustrates a schematic diagram of a tomosynthesis imaging system demonstrating an x-ray imaging device in three example positions in accordance with an embodiment of the presently described technology.

The foregoing summary, as well as the following detailed description of certain embodiments of the presently described technology, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates a schematic diagram of a tomosynthesis imaging system 100 demonstrating an x-ray imaging device 110 in three example positions in accordance with an embodiment of the presently described technology. System 100 includes an x-ray imaging device 110 (illustrated in three example positions, herein referred to as a left, center, and right positions), an x-ray detector 120, and a patient surface 130.

X-ray imaging device 110 includes any device capable of emitting x-rays 114 useful for imaging a patient 132 or patient anatomy from a plurality of positions. For example, device 110 can include an x-ray tube. Imaging device 110 can also include a point of reference 112. Point of reference 112 can be useful in describing one or more paths of motion or trajectories that imaging device 110 may move relative to detector 120 and/or patient surface 130.

X-ray imaging device 110 may include a collimator (not shown). The collimator is configured to adjust a field of view of x-ray imaging device 110. For example, the collimator can include an opening that limits the directions that x-rays 114 emitted from imaging device 110 can travel to those included in a field of view.

X-ray imaging device 110 may also include a collimator motor (not shown). The collimator motor is configured to modify the collimator so as to adjust the field of view. For example, the collimator opening can be configured to modify the size of an opening in the collimator that limits the directions that x-rays 114 emitted from imaging device 110 can travel to those included in a field of view.

The collimator motor may be configured to modify a collimator in imaging device 110 to change a field of view in order to compensate the field of view for a changing distance between imaging device 110 and detector 120 as imaging device 110 moves relative to patient surface 130.

The collimator motor may be configured to modify a collimator in imaging device 110 to change a field of view in order to compensate the field of view for a changing distance between imaging device 110 and detector 120 as imaging device 10 moves relative to patient surface 130 and/or detector 120. For example, in order to obtain a consistent field of view of a patient anatomy, when imaging device 110 is in the center position shown in FIG. 1, the collimator may have a smaller opening for the emitted x-rays 114 than when imaging device 110 is in the left or right positions shown in FIG. 1.

The collimator motor may be configured to modify a collimator in imaging device 110 to change a field of view in order to compensate the field of view for a changing angle between x-rays 114 emitted by imaging device 110 and patient surface 130 as imaging device 110 moves relative to patient surface 130. For example, in order to obtain a consistent field of view of a patient anatomy, when imaging device 110 is in the center position shown in FIG. 1, the collimator may have a smaller opening for the emitted x-rays 114 than when imaging device 110 is in the left or right positions shown in FIG. 1. In addition, a system and/or method such as that described in U.S. patent application Ser. No. 11/088,019, titled "System and Method for Motion and Angulation Profiles in Tomosynthesis" and filed on Mar. 22, 2005, may also be employed to adjust an x-ray beam emitted by imaging device 110 according to movement of imaging device 110.

X-ray detector 120 includes any device capable of receiving x-rays 114 emitted from an x-ray tube and scattered or unscattered by a patient anatomy or other structure. For example, x-ray detector 120 can include a flat panel, solid-state digital x-ray detector. In an embodiment of the present invention, x-ray detector 120 is approximately the same size as traditional x-ray film. For example, detector 120 may be approximately 20 cm by 20 cm, 30 cm by 30 cm, 40 cm by 40 cm, or any other similar dimension.

X-ray detector 120 may include a wall stand detector that is supported and positioned by a wall stand 124 and a wall stand arm 122. Wall stand 124 may be securely connected to a wall or floor of a room in a hospital or clinic. Wall stand arm 122 may be capable of moving relative to wall stand 124 and/or patient surface 130 in order to position x-ray detector 120 in a number of positions. For example, wall stand 124 and wall stand arm 122 may be configured to position x-ray detector 120 so that a surface of detector 120 that receives x-rays 114 emitted from imaging device 110 is parallel to patient surface 130. In system 100, detector 120 is arranged to be perpendicular to patient surface 130.

One or more of wall stand 122 and wall stand arm 124 may be motorized to move detector 120. As described above, wall stand 122 and wall stand arm 124 may then move detector 120 to any one of a number of positions, including parallel or perpendicular to patient surface 130.

In addition, one or more of wall stand 122 and wall stand arm 124 may be motorized to move detector 120 automatically to correspond to a movement of x-ray imaging device 10. For example, one or more of wall stand 122 and wall stand arm 124 may be capable of automatically moving detector 120 so that an x-ray receiving surface of detector 120 is perpendicular to x-rays 114 emitted from imaging device 110 as imaging device 110 moves relative to patient surface 130. In other words, when imaging device 110 is in a position other than the center position of FIG. 1, detector 120 may be moved to be at an angle with respect to a side of patient surface 130. In this way, detector 120 may move so that it always "faces" imaging device 110.

Detector 120 may include an anti-scatter grid. An anti-scatter grid is a mesh of metal of a certain thickness that filters out scattered x-rays. For example, an anti-scatter grid can include a mesh of Tungsten metal of a sufficient thickness to absorb x-rays scattered by an anatomy of patient 132. In traditional tomosynthesis imaging systems (that include an x-ray tube moving up and down, or in a direction perpendicular to the floor), the grid lines of an anti-scatter grid are arranged to be perpendicular to the floor.

The grid lines of the anti-scatter grid used in accordance with detector 120 may be rotated 90° with respect to anti-scatter grids used with traditional tomosynthesis systems. By such rotating, the grid lines are parallel to the floor. In addition, these grid lines are also parallel to long axis 136 of patient surface 130 and to a direction of travel or trajectory of imaging device 110, as described in more detail below.

Patient surface 130 includes any surface capable of supporting a patient 132 or patient anatomy for x-ray imaging. For example, patient surface 130 can be included in a table used to support a patient 132 in a supine position. Patient surface 130 includes a long axis 136. Long axis 136 of patient surface 130 may be parallel to and/or coincide with a length or long axis of a patient 132 on patient surface 130.

Patient surface 130 may be mobile. For example, patient surface 130 may be included in a low-attenuating mobile table. In another example, patient surface 130 is included in a mobile stretcher similar to or such as those used to move patients 132 in and out of ambulances or in emergency trauma situations. By using a mobile patient surface 130, system 100 may be employed in trauma situations. For example, a patient 132 injured and requiring immediate medical care may be placed onto mobile patient surface 130 and moved into a room including system 100 for imaging of the patient's injuries. Patient surface 130 may therefore be capable of supporting a patient in a supine position.

In operation, a patient 132 is placed on patient surface 130. As described above, patient 132 may be placed on a stretcher in an ambulance. Patient surface 130 and patient 132 may then be moved into an emergency trauma area of a hospital, for example.

In accordance with an embodiment of the presently described technology, detector 120 may be positioned so as to be perpendicular to patient surface 130. In addition, detector 120 may be positioned so as to position a patient anatomy to be imaged between detector 120 and imaging device 110 as device 110 moves along path 116.

In order to image one or more anatomies of patient 132, imaging device 110 moves along a trajectory or path parallel to long axis 136 of patient surface 130 while emitting x-rays 114 from a plurality of positions. In other words, imaging device 110 moves along a trajectory defined approximately by path 116 in FIG. 1 while emitting x-rays 114 at the left, center and right positions in FIG. 1. However, device 110 may emit x-rays 114 at additional and/or alternative positions than those shown in FIG. 1.

Imaging device 110 may move along a trajectory or path by any system or method known to those of skill in the art. The movement of imaging device 110 may be referred to as a sweep angle 116, for example.

When detector 120 is perpendicular to patient surface 130, the elevation of imaging device 110 may be approximately equivalent to the elevation of patient surface 130. Therefore, as imaging device 110 moves along path 116, imaging device 110 moves along a side of patient 132 and patient surface 130 and emits x-rays 114 towards the side of patient 132 closest to imaging device 110 at a plurality of positions.

Imaging device 110 may rotate about point of reference 112. For example, point of reference 112 may be a center of imaging device 110. As imaging device 110 moves along path 116, imaging device 110 may rotate towards detector 120. For example, as imaging device 110 moves along path 116, device 110 may rotate so that x-rays 114 emitted by device 110 are directed towards detector 120.

Imaging device 110 may emit low-dose x-rays 114 from one or more of the plurality of positions that it emits x-rays 114. A low-dose x-ray emission includes any x-ray dose less than a traditional x-ray dose used in tomosynthesis imaging systems and methods. For example, a low-dose x-ray may include any dose between that used for traditional x-ray imaging and that used for a CT scan. In another example, a low-dose x-ray may be approximately 5% to 25% of that of a traditional dose used in a CT scan.

Once imaging device 110 has emitted x-rays 114 from a plurality of positions during its movement along path 116 and detector 120 has received these x-rays 114, the received x-rays 114 are converted into a plurality of x-ray images. These images may be referred to as projection images. The projection images are then combined and reconstructed into at least one tomographic plane of anatomy. A computer apparatus (not shown) may be employed to reconstruct the plane of anatomy from the projection images. For example, a computer running a computer software application or program may be used to reconstruct the plane of anatomy.

Figure 2:
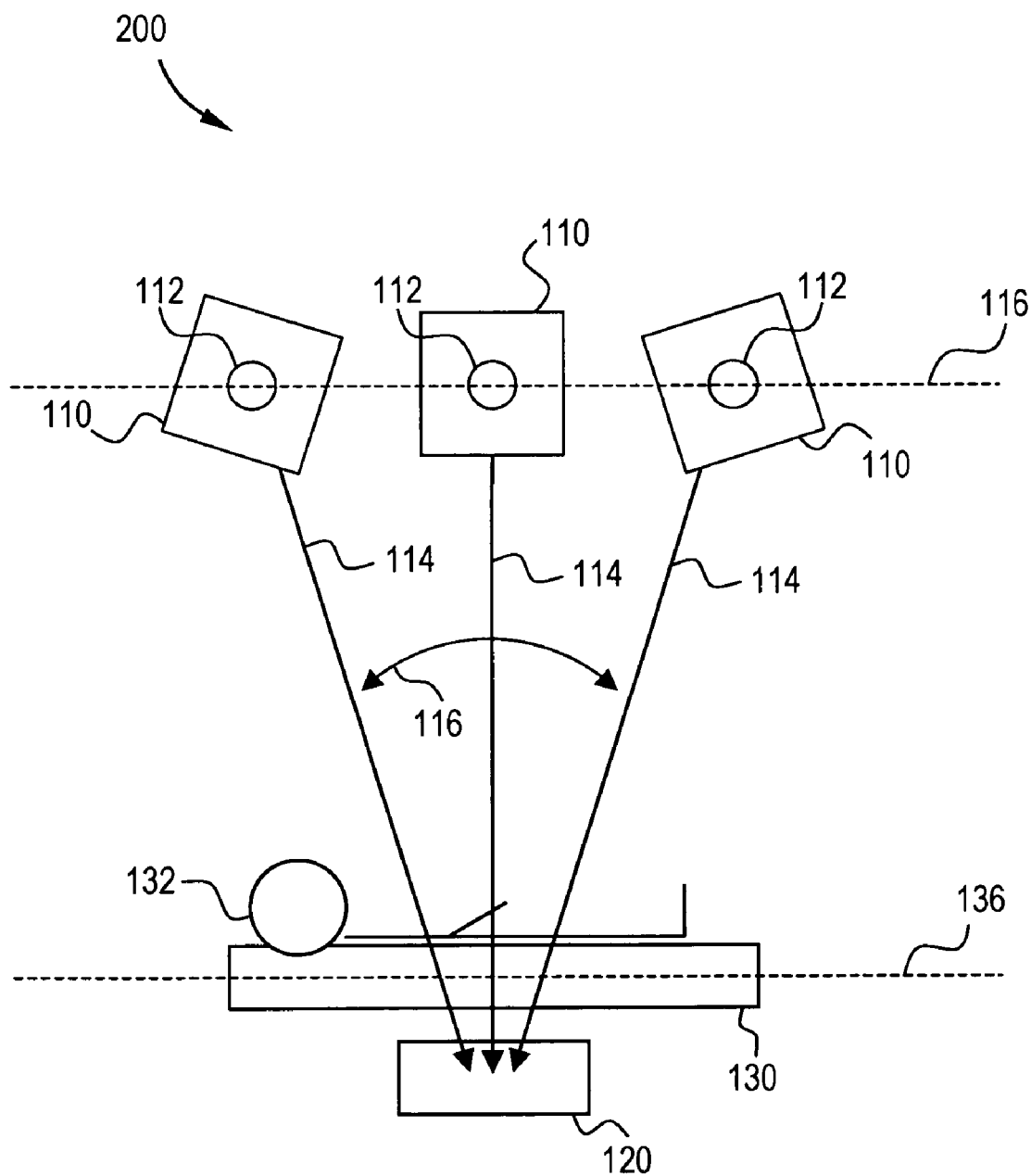
FIG. 2 illustrates a schematic diagram of a tomosynthesis imaging system demonstrating an x-ray imaging device in three example positions in accordance with an embodiment of the presently described technology.

In another embodiment of the presently described technology, detector 120 may be positioned so as to be parallel to patient surface 130. In addition, detector 120 may be positioned so as to position a patient anatomy to be imaged between detector 120 and imaging device 110 as device 110 moves along path 116. FIG. 2 illustrates a schematic diagram of tomosynthesis imaging system 200 demonstrating x-ray imaging device 110 in three example positions in accordance with an embodiment of the presently described technology. System 200 includes the same components as system 100 illustrated in FIG. 1. For example, system 200 includes x-ray imaging device 110 (illustrated in three example positions, herein referred to as a left, center, and right positions), x-ray detector 120, and patient surface 130.

In system 200, detector 120 is arranged to be parallel to patient surface 130. For example, wall stand 124 and wall stand arm 122 may be configured to position x-ray detector 120 so as to position a patient anatomy to be imaged between detector 120 and imaging device 110 as device 110 moves along path 116. For example, detector 120 may be placed below patient surface 130.

In addition, one or more of wall stand 122 and wall stand arm 124 may be motorized to move detector 120 automatically to correspond to a movement of x-ray imaging device 110. For example, one or more of wall stand 122 and wall stand arm 124 may be capable of automatically moving detector 120 so that an x-ray receiving surface of detector 120 is perpendicular to x-rays 114 emitted from imaging device 110 as imaging device 110 moves relative to patient surface 130. In other words, when imaging device 110 is in a position other than the center position of FIG. 1, detector 120 may be moved to be at an angle with respect to a side of patient surface 130. In this way, detector 120 may move so that it always "faces" imaging device 110.

Similar to system 100, in operation with system 200, a patient 132 is placed on patient surface 130. As described above, patient 132 may be placed on a stretcher in an ambulance. Patient surface 130 and patient 132 may then be moved into an emergency trauma area of a hospital, for example.

In order to image one or more anatomies of patient 132, imaging device 110 moves along a trajectory or path parallel to long axis 136 of patient surface 130 while emitting x-rays 114 from a plurality of positions. In other words, imaging device 110 moves along a trajectory defined approximately by path 116 in FIG. 2 while emitting x-rays 114 at the left, center and right positions in FIG. 2. However, device 110 may emit x-rays 114 at additional and/or alternative positions than those shown in FIG. 2.

When detector 120 is parallel to patient surface 130, imaging device 110 moves over patient 132 and patient surface 130. For example, imaging device 110 is at an elevation greater than patient surface 130 and moves over or above patient surface 130. Therefore, as imaging device 110 moves along path 116, imaging device 110 emits x-rays 114 downwards towards patient 132 at a plurality of positions.

Imaging device 110 may rotate about point of reference 112. For example, point of reference 112 may be a center of imaging device 110. As imaging device 110 moves along path 116, imaging device 110 may rotate towards detector 120. For example, as imaging device 110 moves along path 116, device 110 may rotate so that x-rays 114 emitted by device 10 are directed towards detector 120.

Once imaging device 110 has emitted x-rays 114 from a plurality of positions during its movement along path 116 and detector 120 has received these x-rays 114, the received x-rays 114 are converted into a plurality of projection images. As with system 100, the projection images are then combined and reconstructed into at least one tomographic plane of anatomy. A computer apparatus (not shown) may be employed to reconstruct the plane of anatomy from the projection images. For example, a computer running a computer software application or program may be used to reconstruct the plane of anatomy.

In an embodiment of the presently described technology, imaging device 110 may move in a two-dimensional ("2D") trajectory or path with respect to detector 120. For example, path 116 in each of FIGS. 1 and 2 demonstrates a one-dimensional ("1D") trajectory, namely a trajectory approximately along a single direction with respect to detector 120. A 2D trajectory includes movement of imaging device 110 in two directions with respect to detector 120. A 2D trajectory may include a single arc, multiple arcs, a sinusoidal path, a circle, or other 2D shape. In other words, the movement path of imaging device 110 may approximate that of a 2D shape.

In system 100 of FIG. 1, such movement could include moving along path 116 (along a side of patient surface 130) while also moving towards and away from the side of detector 120, for example. In another example, such movement could include moving along path 116 (along a side of patient surface 130) while also moving up and down with respect to detector 120. In another example, such movement could include moving towards and away from a side of patient surface 130 while also moving up and down with respect to detector 120.

In system 100 of FIG. 2, such movement could include moving along path 116 (above patient surface 130) while also moving towards and away from detector 120, for example. In another example, such movement could include moving along path 116 (above patient surface 130) while also laterally across patient surface 130. In another example, such movement could include moving towards and away from a side of patient surface 130 while also laterally across patient surface 130.

In an embodiment of the presently described technology, imaging device 110 may move in a three-dimensional ("3D") trajectory or path with respect to patient surface 130. A 3D trajectory includes movement of imaging device 110 in three directions with respect to patient surface 130. A 3D trajectory can include any 3D shape, such as that of a cube, a sphere, or hourglass shape, for example. In other words, the movement path of imaging device 110 may approximate that of a 3D shape.

In FIG. 1, such movement could include moving along path 116 (along a side of patient surface 130) while also moving towards and away from the side of patient surface 130 and moving up and down with respect to detector 120, for example. In FIG. 2, such movement could include moving along path 116 (above patient surface 130) while also moving towards and away from detector 120 and moving laterally across patient surface 130.

Figure 3:
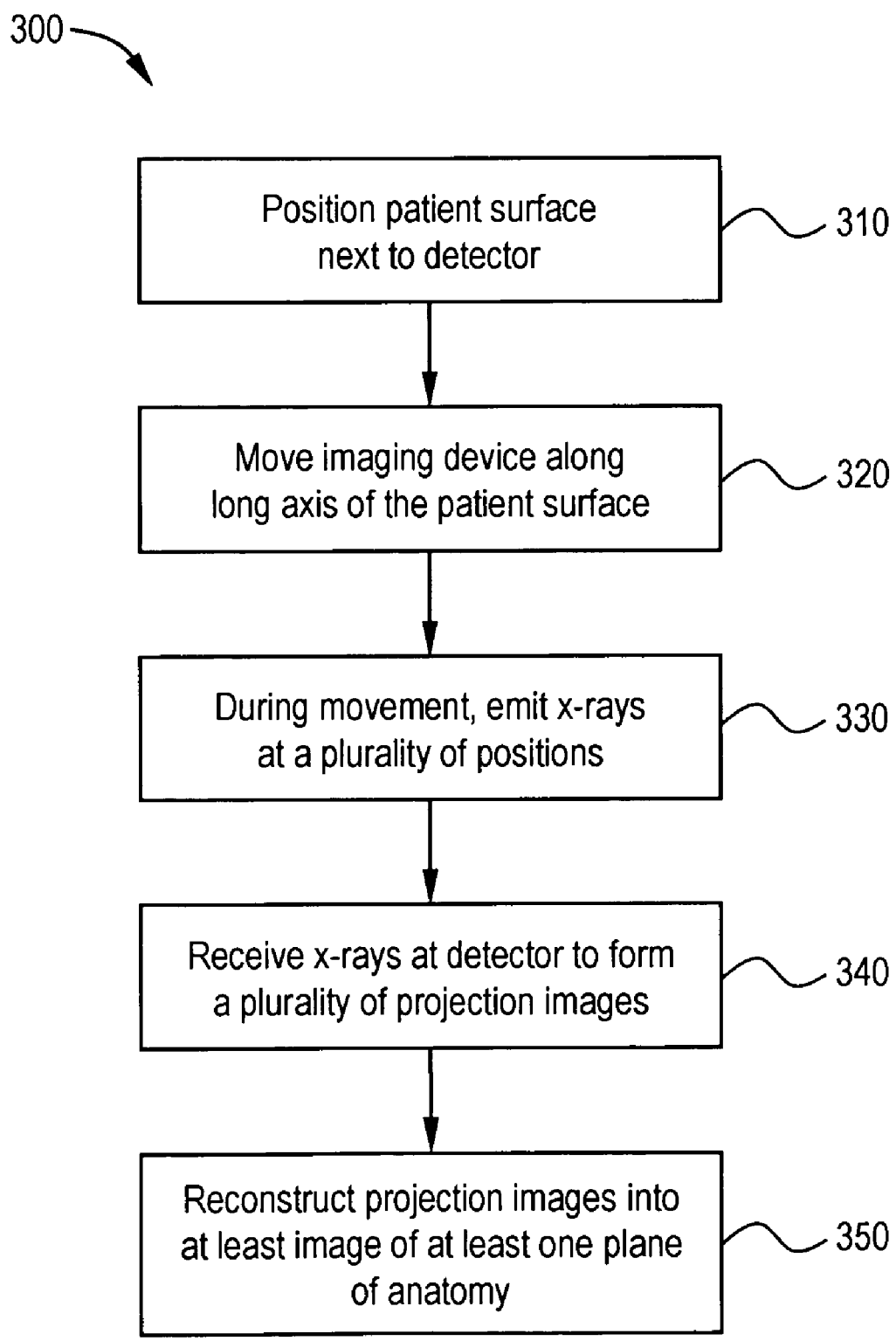
FIG. 3 illustrates a flowchart for a method of employing tomosynthesis to image a patient anatomy according to an embodiment of the presently described technology.

FIG. 3 illustrates a flowchart for a method 300 of employing tomosynthesis to image a patient anatomy according to an embodiment of the presently described technology. First, at step 310, a patient 132 is positioned on a patient surface 130 and both are positioned next to an x-ray detector 120, as described above. For example, a patient 132 may be placed on a mobile table or stretcher in an emergency or trauma situation and moved next to detector 120, as described above. An anatomy of patient 132 may be positioned between detector 120 and imaging device 110.

Next, at step 320, imaging device 110, such as an x-ray tube, is moved along a long axis 136 of patient surface 130. In one embodiment of the presently described technology, imaging device 110 moves along long axis 136 of patient surface 130 along a side of patient surface 130, as described above. In another embodiment, imaging device 110 moves along long axis 136 of patient surface 130 above patient 132 and patient surface 130, also as described above.

In an embodiment of the presently described technology, at step 320 imaging device 110 also moves in additional directions. For example, imaging device 110 may move in a 2D or 3D trajectory with respect to patient surface 130, both as described above.

Next, at step 330, imaging device 110 emits x-rays 114 from a plurality of positions during its movement described in step 320, as described above. The x-rays 114 are emitted towards x-ray detector 120, also as described above. The x-rays 114 emitted may be low-dose x-rays 114, as described above.

In an embodiment of the presently described technology, imaging device 110 may rotate during its movement so that x-rays 114 are emitted towards detector 120, as described above. In addition, detector 120 may rotate towards imaging device 110 as imaging device 110 moves relative to detector 120, also as described above.

Next, at step 340, the x-rays 114 emitted by imaging device 110 are received by detector 120. These x-rays 114 are converted into a plurality of projection images, as described above.

Next, at step 350, the plurality of projection images are reconstructed into at least one image of at least one plane of the patient anatomy, as described above.

The presently described technology provides fast, high resolution images of a patient anatomy. The improved speed and resolution over conventional CT imaging allows the presently described technology to be especially in trauma applications where time is of the essence.

While particular elements, embodiments and applications of the present invention have been shown and described, it is understood that the invention is not limited thereto since modifications may be made by those skilled in the art, particularly in light of the foregoing teaching. It is therefore contemplated by the appended claims to cover such modifications and incorporate those features that come within the spirit and scope of the invention.

What is claimed is:

1. A tomosynthesis imaging system, the system including:
   a stationary x-ray detector adapted to receive x-rays, wherein the x-ray detector is located on a first lateral side of a patient, wherein the patient is in a supine or prone position on a mobile patient surface;
   an x-ray tube adapted to emit x-rays towards the x-ray detector from a plurality of angular positions during a linear movement of the x-ray tube, wherein the linear movement occurs along a second lateral side of the patient, wherein the second lateral side is opposite the first lateral side; and
   a computing apparatus adapted to receive a plurality of projection images based on the x-rays emitted at each of the plurality of positions and received at the x-ray detector, wherein the computing apparatus is farther adapted to reconstruct at least one plane of a patient anatomy from the plurality of projection images.

2. The system of claim 1, wherein the mobile patient surface is adapted to move the patient into the imaging system, wherein the mobile patient surface is not fixed to one or more of a floor, a wall, a ceiling, or the imaging system.

3. The system of claim 1, wherein the mobile patient surface is a stretcher.

4. The system of claim 1, wherein the patient anatomy includes a vertebra of the patient.

5. The system of claim 1, wherein the x-ray tube is adapted to move along the second lateral side by moving along a side of the mobile patient surface at an elevation approximately equal to the mobile patient surface.

6. The system of claim 1, wherein the x-ray tube is adapted to move along the second lateral side by moving above the mobile patient surface at an elevation greater than the mobile patient surface.

7. The system of claim 1, wherein the x-ray tube is adapted to move in one or more of a one-dimensional ("1D") trajectory, a two-dimensional ("2D") trajectory and a three-dimensional ("3D") trajectory relative to the x-ray detector.

8. The system of claim 1, further including:
a collimator adapted to adjust a field of view; and
a collimator motor adapted to modify the collimator in order to adjust the field of view.

9. The system of claim 8, wherein the collimator motor is adapted to change a size of an opening in the collimator in order to compensate for one or more of:
a changing distance between the x-ray tube and the x-ray detector; and
a changing incident angle between the x-rays and the x-ray detector.

10. A method for employing tomosynthesis to image a patient anatomy, the method including:
moving an x-ray tube linearly along a second lateral side of a patient, wherein the patient is in a supine or prone position on a mobile patient surface;
emitting x-rays from the x-ray tube towards a stationary x-ray detector from a plurality of angular positions during the linear movement of the x-ray tube, wherein the x-ray detector is adapted to receive x-rays, wherein the x-ray detector is located on a first lateral side of the patient, wherein the second lateral side is opposite the first lateral side;
receiving a plurality of projection images based on the x-rays emitted at each of the plurality of positions and received at the x-ray detector; and
reconstructing at least one plane of a patient anatomy from the plurality of projection images.

11. The method of claim 10, wherein the mobile patient surface is adapted to move the patient into the imaging system, wherein the mobile patient surface is not fixed to one or more of a floor, a wall, a ceiling, or the imaging system.

12. The method of claim 10, wherein the mobile patient surface is a stretcher.

13. The method of claim 10, wherein the patient anatomy includes a vertebra of the patient.

14. The method of claim 10, wherein the x-ray moves along the second lateral side at an elevation approximately equal to the mobile patient surface.

15. The method of claim 10, wherein the x-ray tube moves along the second lateral side at an elevation greater than the mobile patient surface.

16. The method of claim 10, wherein the x-ray tube moves in one or more of a one-dimensional ("1D") trajectory, a two-dimensional ("2D") trajectory and a three-dimensional ("3D") trajectory relative to the x-ray detector.

17. The method of claim 10, further including:
adjusting a field of view by modifying a collimator connected to the x-ray tube.

18. The method of claim 17, wherein the adjusting step includes changing a size of an opening in the collimator in order to compensate for one or more of:
a changing distance between the x-ray tube and the x-ray detector; and
a changing incident angle between the x-rays and the x-ray detector.

* * * * *